(12) United States Patent  
Riley (10) Patent No.: US 7,066,329 B2  
(45) Date of Patent: Jun. 27, 2006

(54) MEDICAL INSTRUMENT HOLDING AND PRESENTATION SYSTEM

(75) Inventor: Edward D. Riley, Falmouth, ME (US)

(73) Assignee: Riley Medical, Inc., Auburn, ME (US)

( * ) Notice: Subject to any disclaimer, the term of this patent is extended or adjusted under 35 U.S.C. 154(b) by 329 days.

(21) Appl. No.: 10/675,186

(22) Filed: Sep. 30, 2003

(65) Prior Publication Data

US 2005/0016886 A1   Jan. 27, 2005

Related U.S. Application Data

(60) Provisional application No. 60/488,892, filed on Jul. 21, 2003.

(51) Int. Cl.
*B65D 85/20* (2006.01)

(52) U.S. Cl. ............... 206/443; 206/369; 206/370; 206/63.5; 206/562; 422/297

(58) Field of Classification Search ............ 206/63.5, 206/363, 364, 365, 439, 443, 562, 564, 369, 206/370; 211/74; 422/297, 298
See application file for complete search history.

(56) References Cited

U.S. PATENT DOCUMENTS

| | | | | |
|---|---|---|---|---|
| 2,612,261 A | * | 9/1952 | Percopo | .................. 206/529 |
| 3,643,812 A | * | 2/1972 | Mander et al. | ............... 211/74 |
| 4,050,894 A | | 9/1977 | Genis | |
| 4,253,830 A | * | 3/1981 | Kazen et al. | .................. 433/77 |
| 5,069,336 A | * | 12/1991 | Mauthe | ..................... 206/219 |
| 5,172,810 A | | 12/1992 | Brewer | |
| 5,518,115 A | | 5/1996 | Latulippe | |
| 5,603,899 A | * | 2/1997 | Franciskovich et al. | ..... 422/100 |
| 5,628,400 A | * | 5/1997 | Feder | ..................... 206/379 |
| 5,792,426 A | * | 8/1998 | Portmann et al. | ........... 422/102 |
| 5,843,388 A | | 12/1998 | Arroyo et al. | |
| 5,850,917 A | * | 12/1998 | Denton et al. | .............. 206/366 |

(Continued)

FOREIGN PATENT DOCUMENTS

WO    WO 0057810    5/2000

*Primary Examiner*—David T. Fidei
(74) *Attorney, Agent, or Firm*—John F. McKenna; Cesari and McKenna, LLP (57) ABSTRACT

A medical instrument holder assembly comprises a holder module base including first tubes defining first passages, each first passage having open upper and lower ends, at least one first web connecting and supporting those first tubes in parallel spaced-apart relation so that a fluid can circulate around and between the first tubes, and instrument supports underlying the first tubes for supporting medical instruments placed in the first passages while allowing a fluid to circulate through those passages. The holder assembly also includes a cover for seating on the base and covering the instruments supported thereby, the cover being formed by second tubes defining second instrument receiving passages, each second passage having upper and lower open ends, the lower ends having the same cross-sections as the upper ends of the first passages. At least one second web connects and supports the second tubes in parallel spaced-apart relation so that when the cover is seated on the base, the corresponding first and second passages are co-linear. Preferably, the assembly also includes an outer sterilization/storage case for containing a plurality of covered holder module bases packed closely together and a presentation tray capable of supporting a plurality of the holder module bases so that the instruments therein can be grasped easily by a surgeon.

20 Claims, 7 Drawing Sheets

U.S. PATENT DOCUMENTS

| | | | |
|---|---|---|---|
| 5,967,318 A * | 10/1999 | Rosler | 206/372 |
| 6,019,225 A * | 2/2000 | Kalmakis et al. | 206/563 |
| 6,048,503 A * | 4/2000 | Riley et al. | 422/298 |
| 6,098,802 A * | 8/2000 | Asa et al. | 206/443 |
| 6,349,827 B1 * | 2/2002 | Feder | 206/373 |
| 2005/0019237 A1 * | 1/2005 | Riley | 422/297 |

* cited by examiner

MEDICAL INSTRUMENT HOLDING AND PRESENTATION SYSTEM

CROSS-REFERENCE TO RELATED APPLICATION

This application claims the benefit of Provisional Application No. 60/488,892, filed on Jul. 21, 2003.

BACKGROUND OF THE INVENTION

1. Field of the Invention

This invention relates to a system or assembly for holding selected sets of medical instruments or tools during sterilization and storage prior to use and for presenting them in a logical order when they are being used to perform a particular surgical procedure.

Different surgical procedures require the use of different sets of instruments or tools, the number of tools in the set depending upon the complexity of the procedure. For example, for a tooth implant, the instrument or tool set may include a twist drill, a drill extension, a driver, and various size screws. Sometimes the set includes duplicate tools in the event one breaks. If more than one implant is involved in the procedure, more and/or different tools may be required than for a single implant. Thus prior to a particular surgical procedure, the surgeon determines or knows from experience which instruments will be required. Those instruments are gathered together as a set, placed in a container which is packaged in a plastic package and then sterilized either chemically or in an autoclave. The packaged instrument set is then stored in that sterile condition until ready for use. When the surgeon is ready to perform the procedure, the container is brought to the operating room and opened exposing the still sterile instruments therein. At the end of the procedure, the instruments may be returned to the container and sent to a cleaning and sterilization facility.

2. Description of the Prior Art

The basic concept of organizing surgical instruments or tools into sets for subsequent sterilization, storage and presentation is not new; see for example U.S. Pat. No. 5,518,115. Shown there is a perforated sterilization container including a removable cover and an internal tray or rack for supporting a set of medical instruments in an organized manner. More particularly, the instruments are vertically supported in grommets mounted to the tray at spaced-apart locations thereon. Graphics may be imprinted on the tray to identify the instruments at particular locations in the container.

While that assembly is satisfactory in many respects, it is disadvantaged in that it does not take into account the fact that the numbers of instruments in the sets required for different procedures may vary over a wide range. For example, perhaps only three or four tools may be required to perform a single tooth implant while many more tools may be needed for a procedure involving multiple tooth implants. Therefore, the "one size fits all" container disclosed in the above patent must be dimensioned to accommodate the largest set of tools or instruments required for the most complex surgical procedure. This means that if the container is used to sterilize and store a small set of instruments, the container would be mostly empty and thus waste sterilizer and shelf space. Likewise, that container may be too large to fit in the small sterilizers found in some physician offices and clinics.

Another disadvantage of that patented container is that the grommets which support the instruments must be removed from the internal tray following surgery because blood and tissue collect in the spaces between the grommets and the tray. This adds to the cost of cleaning and maintaining that container assembly.

SUMMARY OF THE INVENTION

Accordingly, this invention aims to provide an improved system for sterilizing, storing and presenting sets of medical instruments.

Another object of the invention is to provide a system of this type which is modular and can thus accommodate different size instrument sets.

Another object of the invention is to provide a medical instrument holder module for containing different length instruments during sterilization and storage.

Another object of the invention is to provide a modular sterilization and storage container assembly for medical instruments and the like.

A further object of the invention is to provide a system and an assembly as described above which are relatively easy and inexpensive to make in quantity.

Other objects will, in part, be obvious and will, in part, appear hereinafter. The invention accordingly comprises the features of construction, combination of elements and arrangement of parts which will be exemplified in the following detailed description, and the scope of the invention will be indicated in the claims.

Briefly, my system or assembly comprises one or more instrument holder modules, an outer case for receiving and supporting a plurality of such modules during sterilization and storage, and a tray for presenting the modules during a surgical procedure so that the instruments therein are readily accessible to the surgeon performing the procedure.

Each holder module includes a base formed with a plurality of spaced-apart tubes forming recesses or passages for vertically supporting axially symmetric instruments or tools having different lengths, such as drills, drivers, picks, screws, etc. Each holder module also includes a cover formed similarly to the base which, when coupled to the base, covers and captures the instruments within the module. As we shall see, the module is designed so that a sterilant, such as steam, is free to circulate around and through the tubes to sterilize the instruments therein.

The second component of my system or assembly, namely the outer sterilization/storage case, comprises a bottom section and a removable cover section therefore, both of which are dimensioned and designed so that a maximum number of holder modules can be packed together in a case of minimum volume. A multiplicity of holes are provided in the outer case so that a sterilant can be circulated throughout the case and its contents.

The third, i.e. tray, component of my system is adapted to releasably retain the bases of a plurality of holder modules during a surgical procedure so that the instruments supported by the bases are properly organized and readily accessible to the surgeon. Preferably, graphics are printed on the tray to identify the instruments at particular locations in the module bases supported by the tray.

It is a feature of the invention that the components of my assembly can be used in different ways. For example, if a particular surgical procedure requires the use of only a small set of tools or instruments, that set may be placed in a single holder module and then packaged, sterilized and stored until needed. When required, the holder module may be brought to the operating room and opened exposing the still sterile instruments supported by the base.

On the other hand, if a procedure requires a larger set of instruments or tools, a plurality of holder modules packed together in the outer case may be sterilized and stored until needed. When it is time to use those instruments, the case and its contents may be brought to the operating room and the holder modules removed from the case and engaged to the presentation tray following which the modules may be opened to reveal the instruments therein which are organized in accordance with graphics on the tray and/or on the module.

Thus, it will be appreciated that while the holder modules are packed tightly together within the outer case in order to minimize the space taken up by that assembly in the sterilizer or on the shelf, the modules may be spread out over the larger area surface of the presentation tray so that the instruments therein may be grasped easily by the surgeon.

All of the components of my system may be simple, unitary, molded plastic parts which are easy and inexpensive to make in quantity and which do not require initial assembly or subsequent disassembly for cleaning purposes.

BRIEF DESCRIPTION OF THE DRAWINGS

For a fuller understanding of the nature and objects of the invention, reference should be made to the following detailed description taken in connection with the accompanying drawings, in which.

DETAILED DESCRIPTION OF ILLUSTRATIVE EMBODIMENTS

Figure 1:
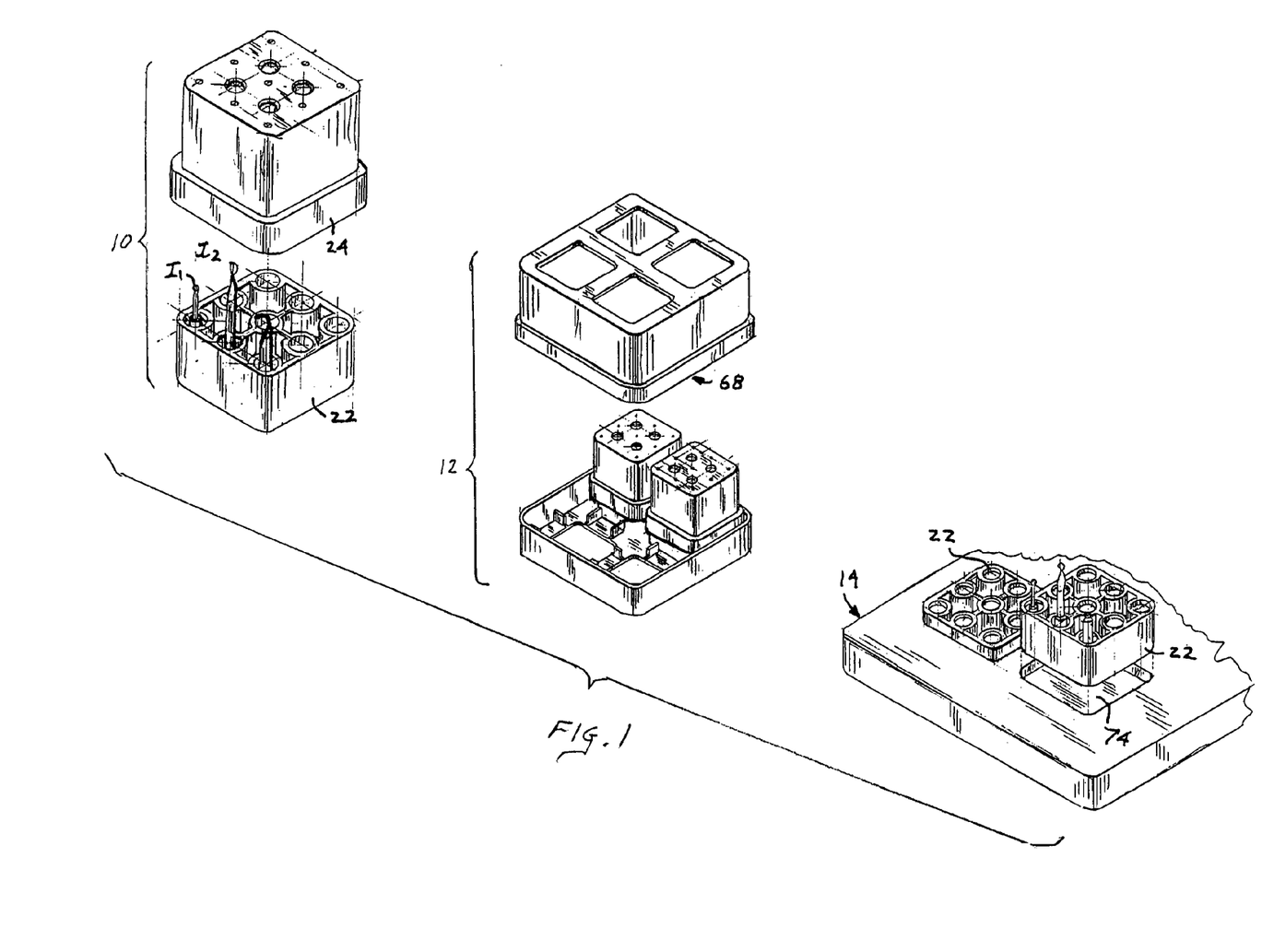
FIG. 1 is an exploded perspective view showing the components of a medical instrument holding and presentation system according to the invention.

Referring to FIG. 1 of the drawings, my system or assembly comprises three main components, namely one or more instrument holder modules shown generally at 10, an outer sterilization/storage case shown generally at 12 for containing modules 10 during sterilization and storage, and a presentation tray shown generally at 14 for supporting the modules in an orderly manner so that the instruments therein are readily accessible to a surgeon who will use those instruments in order to perform a particular operation. Preferably, all of the system components are made of a suitable rigid plastic material able to withstand sterilization, e.g. polyphenylsulfone.

Figure 2:
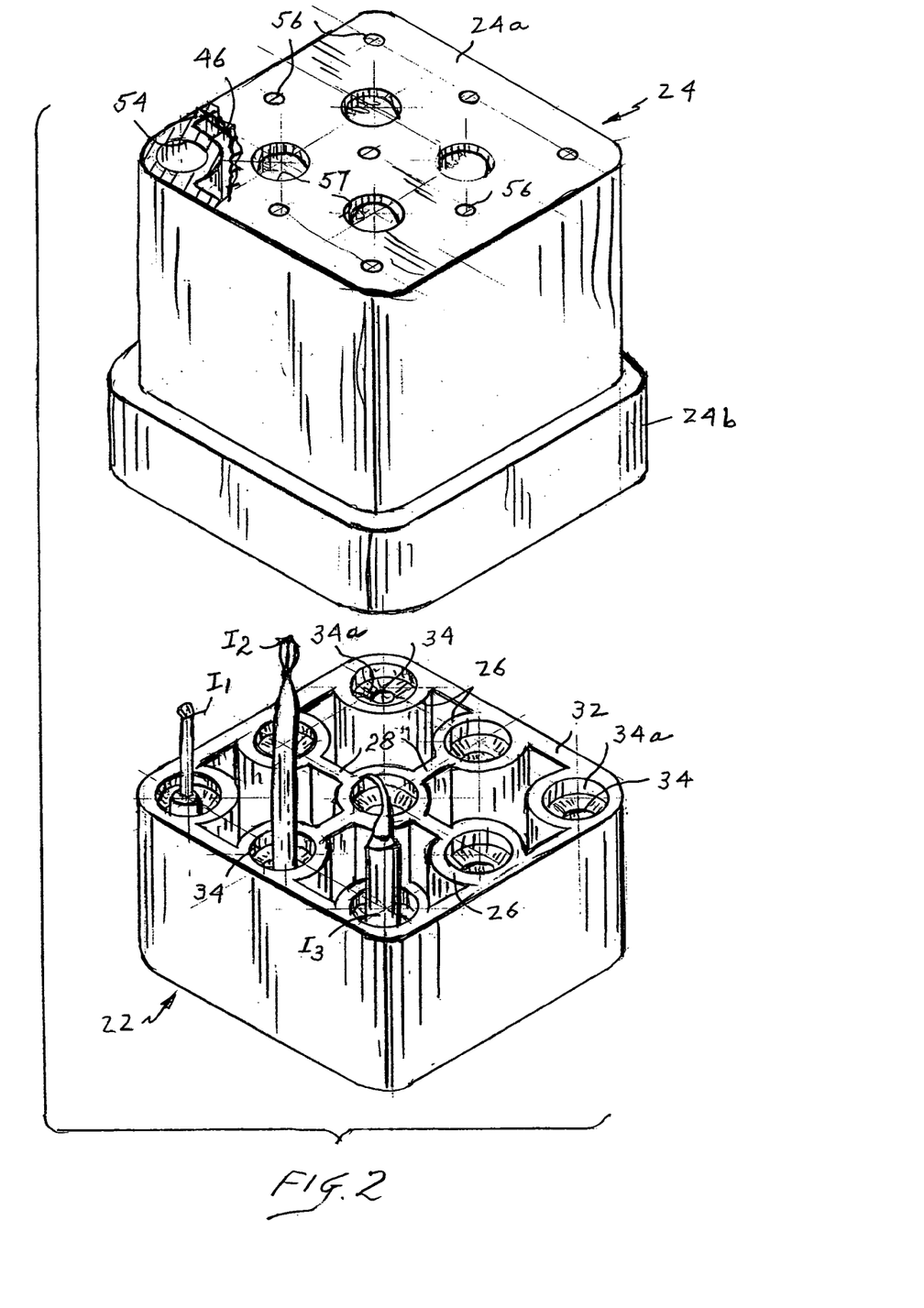
FIG. 2 is a similar view on a larger scale and with parts broken away showing the holder module component of the FIG. 1 system.
Figure 3A:
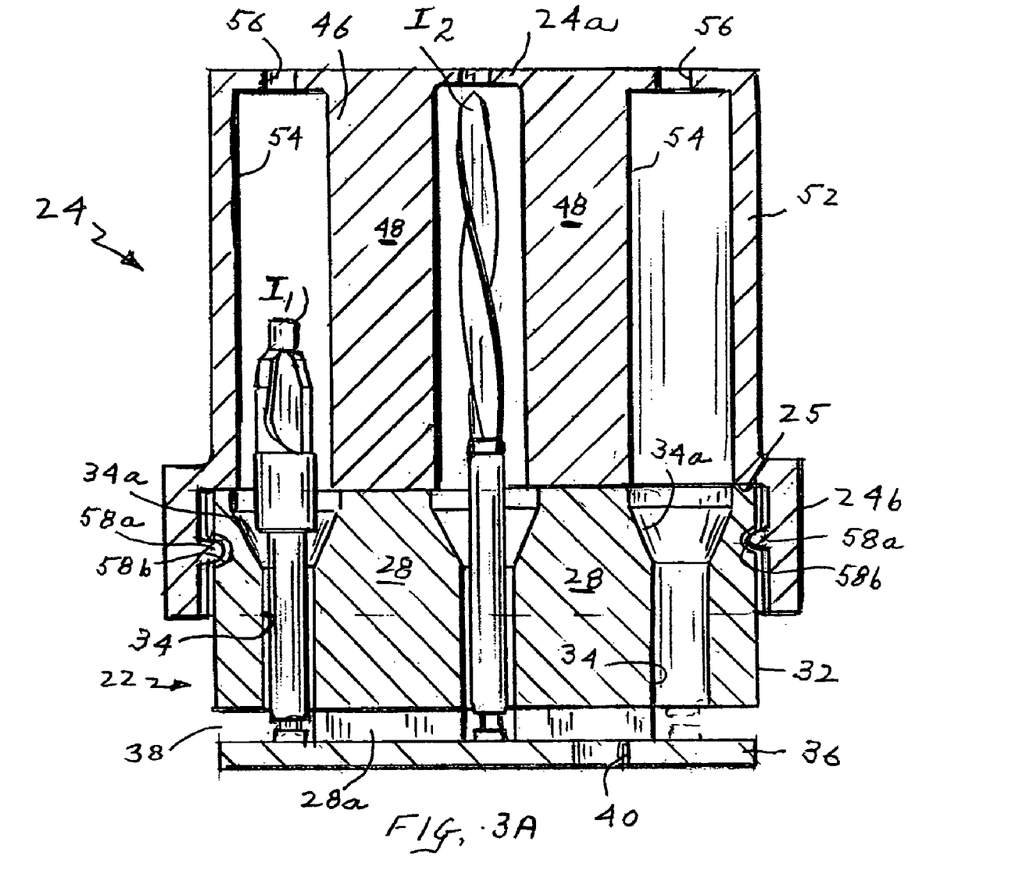
FIG. 3A is a cross-sectional view of the FIG. 2 holder module.

As shown in FIGS. 2 and 3A, each module 10 includes a base 22 and a cover 24 that may be removably engaged over the base. Base 22 is preferably a unitary molded plastic part formed with a plurality of vertical tubes 26 some of which may be interconnected by webs 28 and all of which are surrounded by a peripheral web or wall 32. Base 22 is open at the top and bottom and between the webs and tubes so that a fluid sterilant, e.g. steam, can circulate around and through the tubes to sterilize the instruments therein.

The illustrated base has nine tubes arranged in columns and rows. It should be understood, however, that the base may be designed with more or fewer tubes depending upon the number of instruments to be supported by the base. Typically, the base has 1, 2, 3 . . . n columns of equally spaced-apart tubes. Also, while the illustrated tubes are cylindrical, they could have other shapes.

Each tube has an axial passage 34 which extends the full height of the tube and is open at both ends. The passage 34 cross-section is sized to enable the passage to receive the elongated instruments and tools $I_1$, $I_2$, $I_3$, etc. customarily used to perform surgical procedures such as dental implants, root canals, anthroscopic surgery and the like. These instruments and tools may include drills, drivers, holders, picks, grinding tools, placement tools as well as various fasteners such as screws. Preferably, the upper entry ends 34a of the passages 34 are flared or formed as funnels to facilitate inserting instruments or tools into the passages so that they will be supported vertically by the base.

Figure 3B:
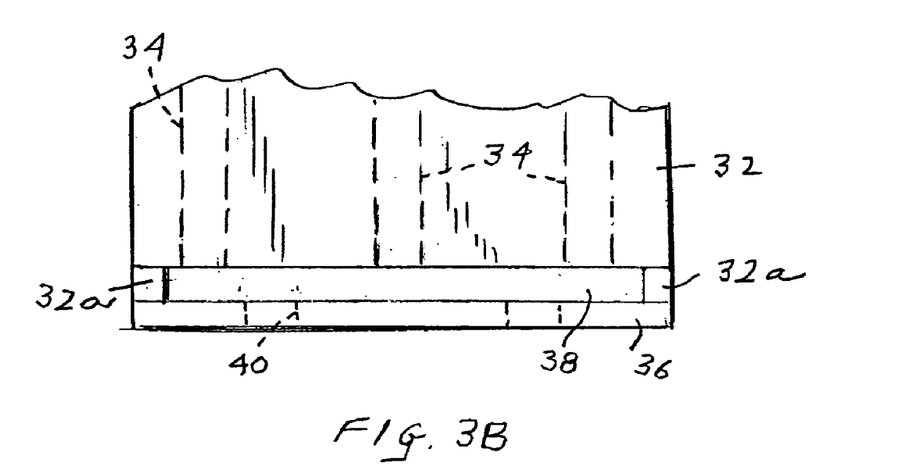
FIG. 3B is a fragmentary side elevational view of the FIG. 2 holder module.

Some instruments such as $I_1$ have enlarged hubs which prevent their dropping from the lower ends of passages 34, other tools such as $I_2$ and $I_3$ do not. Therefore, means are provided at the bottom of base 22 for positively supporting the lower ends of the instruments. More particularly as shown in FIGS. 3A and 3B, the webs 28 between tube 26 and the front and rear segments of wall 32 have extensions 28a and 32a, respectively, which extend down somewhat below the bottoms of the tubes and connect to a bottom wall 36. Thus the instruments I are supported by that wall, yet a slot or gap 38 exists between wall 36 and the bottoms of tubes 26 through which a sterilant may flow into the various passages 34 in order to sterilize the instruments therein.

If desired, larger holes 40 (FIG. 3A) may be provided in bottom wall 36 between the tubes 26 to optimize sterilant circulation through the module.

Still referring to FIGS. 3A and 3B, the cover 24 is adapted to engage over base 22 so as to cover all of the instruments in the base. The cover may be a molded plastic part structurally similar to the base in that it may be formed with a plurality of tubes 46, some connected together by webs 48, and all surrounded by a peripheral side web or wall 52. The cylinders 46 define passages 54 which are positioned and designed so that when the cover 24 is seated on the base 22, the passages 54 are collinear with, and have the same cross-section as, the entry ends 34a of passages 34 in the base.

Typically cover 24 is taller or higher than the base so that it can accommodate the longest instrument I likely to be supported in the base.

Cover 24 is provided with a top wall 24a formed with small holes 56 at the tops of the passages 54 so that a sterilant can circulate through those passages. Preferably, the holes 54 are smaller than the cross-sections of the instruments I so that if the holder module 10 should be inverted, the instruments will not fall out through those holes.

If desired, additional larger holes 57 may be provided in the top wall 24a between the tubes 46 to optimize fluid circulation through the module.

In order to secure cover 24 to base 22, the cover is provided with a skirt 24b which is adapted to surround base 22 and which forms an overhang 25 (FIG. 3A) which can rest on the upper edge of wall 32. Preferably, means are provided for releasably securing skirt 24b to base 22. The securement means may take the form of interfitting surfaces 58a and 58b on skirt 24b and the base wall 32 as shown. Alternatively, the skirt 24b may simply have a tight friction fit about the base.

The holder module 10 with base 22 is able to hold a plurality of instruments I so that they can be sterilized in a small sterilizer. When packaged and sterilized, the instruments in holder 10 will remain in a sterile condition for a relatively long time until needed.

Figure 4:
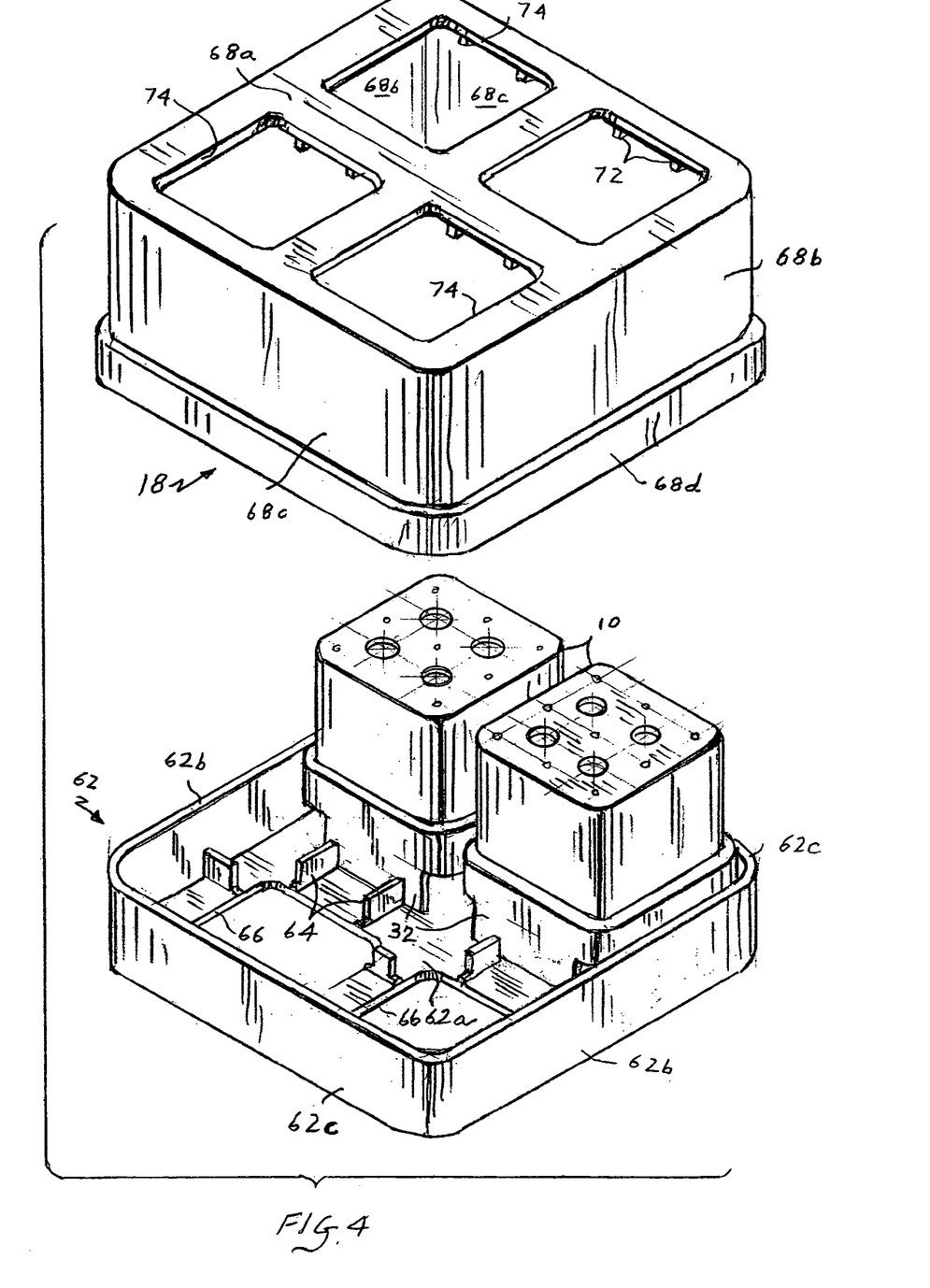
FIG. 4 is an exploded perspective view showing the outer case component of the FIG. 1 system.

Referring now to FIGS. 1 and 4, the outer storage/sterilization case 12 of my system comprises a molded plastic bottom section 62, having a bottom wall 62a, a pair of opposite side walls 62b, 62b and a pair of opposite end walls 62c, 62c. Section 62 is shaped and arranged to support in a closely packed-together fashion, a plurality of the holder modules 10. Preferably, a plurality of resilient retainer tabs 64 project up from bottom wall 62a for locating and retaining the modules 10 within the bottom section. In other words, the tabs resiliently engage the sides of the module base walls 32 in order to positively retain the modules in place.

Preferably also, large openings 66 are provided in the bottom wall 62a which underlie the various modules in the bottom section so that a sterilant can circulate freely through the modules in the case.

The outer case 12 also includes a cover section 68 which is shaped and arranged to seat on the bottom section 62. Cover section includes a top wall 68a, a pair of opposite side walls 68b, 68b and a pair of opposite end walls 68c, 68c. The top wall 68a of the cover section has depending resilient retainer tabs 72 which complement the tabs 64 of the bottom section to help position and hold the holder modules 10 within the case when the cover section 68 is seated on the section 62. Relatively large openings 74 may be provided in that wall so that when the cover section is seated on the bottom section, fluid can circulate through the case.

Finally, the cover 68 is formed with a skirt 68d, similar to skirt 24b of module 10, which engages around the upper edge margin of the bottom section 62 when the cover section is seated on the bottom section. Interfitting or frictionally engaging surfaces such as those of module 10 may releasably secure the cover section to the bottom section.

The inclusion of the case 12 in the system allows a larger set of instruments I housed in a plurality of holder modules 10 to be packaged and sterilized at the same time, with that larger instrument set being maintained in a sterile condition until needed. It should be understood that the case 12 may be sized to hold any number of instrument-containing modules necessary to perform a procedure of any complexity, the objective being to package a given set of contained instruments so that the set takes up a minimum amount of space in a sterilizer or on the shelf.

Figure 5:
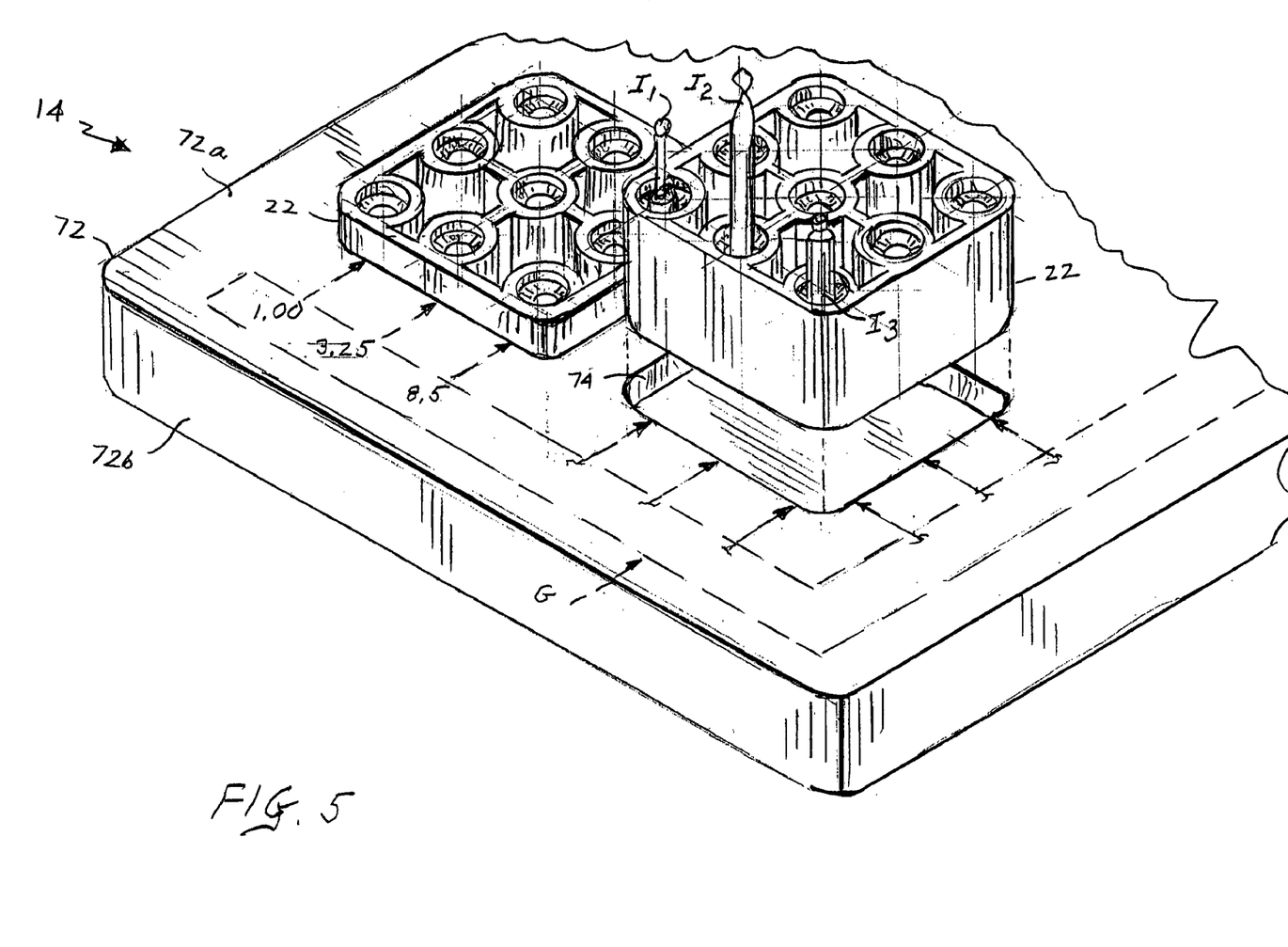
FIG. 5 is a perspective view showing the presentation tray component of the FIG. 1 system.

Referring to FIGS. 1 and 5, the final component of my system, namely the presentation tray 14, is a simple molded plastic shell 72 having a top wall 72a and a depending peripheral skirt 72b extending down from wall 72a. Wall 72a is formed with a plurality of depressions or recesses 74 capable of receiving and retaining a plurality of holder modules 10. The surface area of tray 14 is large enough so that the module bases 22 are spread apart and presented in an organized way so that the instruments therein can be viewed and grasped easily by a surgeon or other operating room personnel.

Preferably, the top wall 72a of tray 14 carries printed graphics, indicated generally at G, which identify the instruments or tools in the modules 10 carried by tray 14.

My system, comprising one or more holder modules 10, outer case 12 and tray 14, may be packaged as a unit and sold to hospitals and clinics where complex procedures involving the use of large instrument sets are performed on a routine basis. On the other hand, the holder modules 10 may also be packaged and sold separately to individual physicians and smaller clinics or offices where smaller sets of instruments are used and where sterilizer space may be at a premium.

Figure 6:
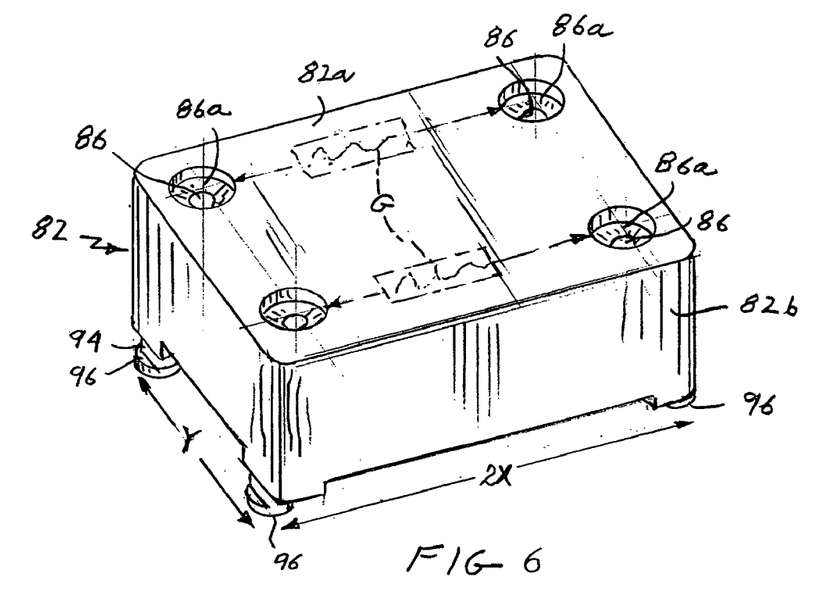
FIG. 6 is a perspective view from above of a second holder module base embodiment for the FIG. 1 system.
Figure 7:
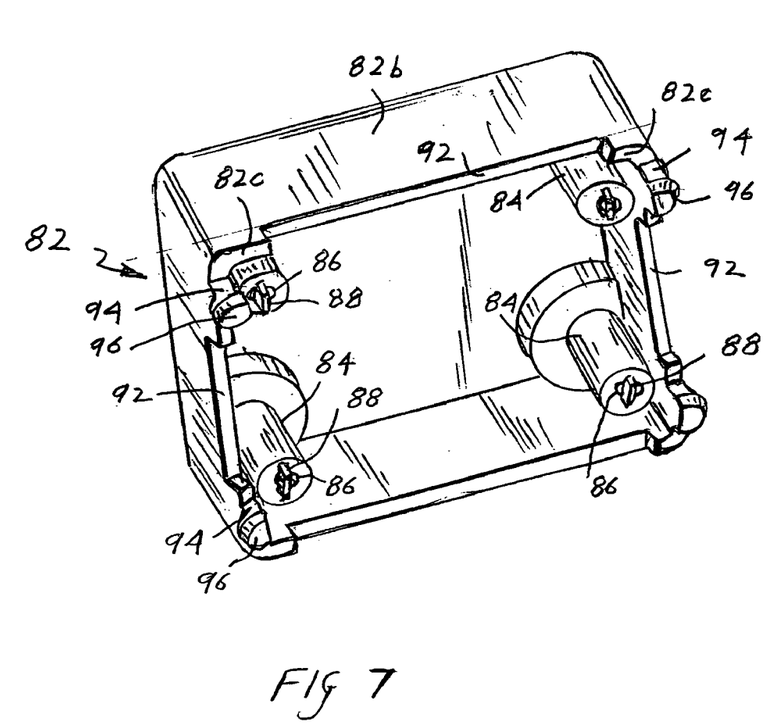
FIG. 7 is a similar view from below of that embodiment.

FIGS. 6 and 7 show generally at 82 a second module base embodiment. Base 82 is provided with a top wall 82a on which may be printed graphics G which describe or identify the various instruments supported by the base. Like base 22 described above, base 82 is formed with a plurality of tubes 84 preferably arranged in columns and rows and surrounded by a peripheral side wall or web 82b which extends down from top wall 82a. Since there are only four tubes 84 in base 82, they are located at the corners of the base and no reinforcing webs are needed between the tubes. As before, each tube defines a lengthwise passage 86 having a flared or funnel-shaped entrance end 86a except, in this case, end 86a opens into the top wall 82a of the base.

As best seen in FIG. 7, the passage 86 in each tube extends all the way through the lower end of the tube. But unlike the base 22, the base 82 has no bottom wall. Rather, the lower end of each tube 84 is formed with an integral bridge 88 which diametrically bridges the lower end of the passage 86 formed by that tube so that the bridge partially occludes that passage. Thus, when an instrument is inserted into a passage 86, the lower end of that instrument is supported by the corresponding bridge 88. However, a sterilant is still able to flow into the lower end of each passage 86 on either side of the corresponding bridge 88.

Still referring to FIG. 7, the side wall or web 82b of base 82 extends down from wall 82a so that the lower edge 82c of that side wall is lower than the lower ends of tubes 84. Thus, when edge 82c rests on a supporting surface, the lower ends of the passages 86 are spaced above that surface so that sterilant can be circulated through those passages. To optimize that circulation, the lower edge 82c may be provided with one or more notches 92.

For reasons that will become apparent, base 82 is formed with short rectangular legs 94 which extend down at the four corners of the base. Also, laterally extending semicircular feet 96 are provided at the lower ends of the legs. Thus the legs and feet together form keys which enable the base 82 to be releasably secured to a presentation tray as will be described presently.

The base 82 may be used in conjunction with a cover similar to cover 24 to fully enclose the instruments supported by the base. Of course, the cover is designed to compliment the base in that it is provided with instrument-receiving passages 54 (FIG. 3A) which, when the cover is seated on the base, are co-linear with the passages 86 in the base.

Figure 8:
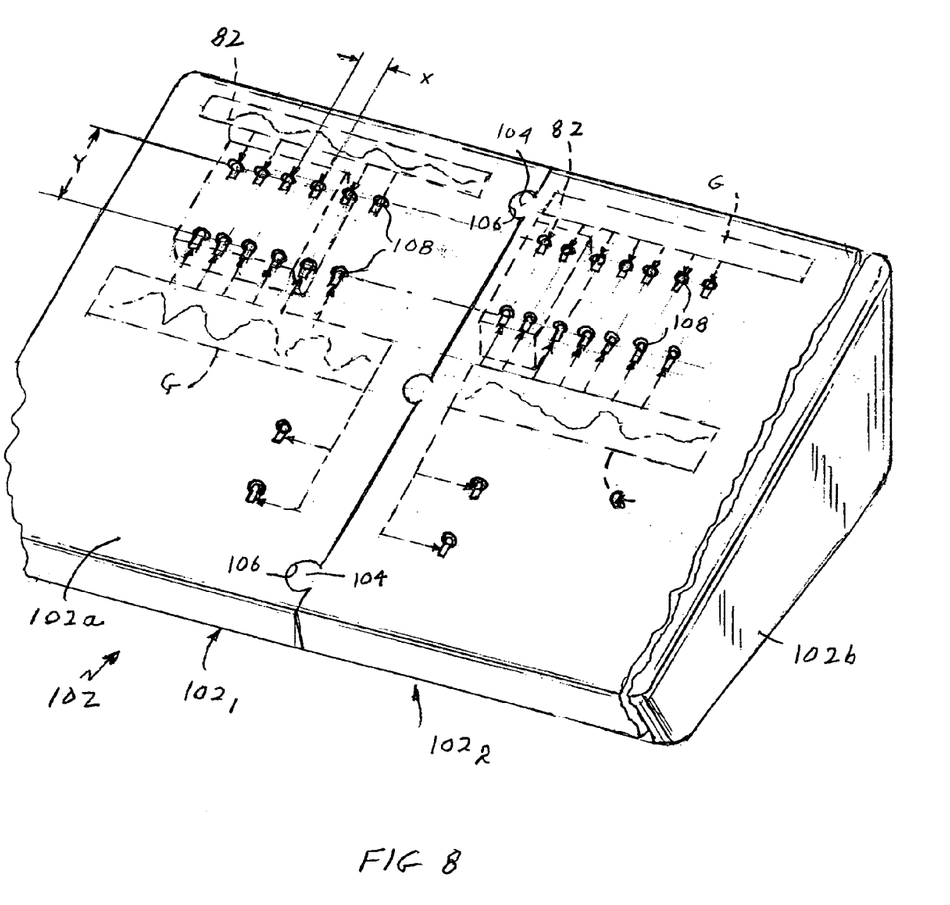
FIG. 8 is a second tray embodiment for presenting instruments or tools in the FIGS. 6 and 7 module bases.

Refer now to FIG. 8 which shows a presentation tray 102 which is adapted to releasably support a plurality of the module bases 82 so that the instruments in those bases are arranged in a logical manner and may be grasped easily by a surgeon. Tray 102 comprises a top wall 102a and a side wall or skirt 102b which extends down from the top wall. Preferably, that skirt is cut on a bias so that the top wall 102a is inclined and more or less faces the person using the instruments supported on the tray.

In order to minimize the space occupied by tray 102 during shipping and storage, the tray may be composed of a plurality of sections $102_1$ and $102_2$ which may be releasably secured together. In the illustrated tray 102, the securement is accomplished by mating keys 104 and keyways 106 formed at opposing edges of tray sections 102₁ and 102₂ respectively, enabling the tray sections to be keyed together like puzzle pieces. Alternatively, the tray sections may be connected by a hinge enabling the tray to be folded up into a compact package.

Still referring to FIG. 8, the tray top wall 102a is provided with rows of keyholes 108 which are positioned to be keyed into by module bases 82 of various widths. In other words, the keyholes 108 are arranged so that the feet 96 of a module base 82 may be aligned with and keyed into selected ones of those keyholes to releasably lock the base to the tray. Thus, the illustrated tray 102 is shown with two rows of keyholes 108. The spacing Y between the rows corresponds to the distance between the front and rear feet 96 of module 82, while the distance X between the keyholes 108 in each row of key holes corresponds to the distance between the side legs of the smallest module 82, i.e. one that has a single column of instrument-receiving passages 86. That smallest module 82 can key into two side-by-side columns of keyholes 108 as shown by the module 80 mounted to the tray section 102₂. On the other hand, a wider module 82 having three columns of passages 86 might be keyed to the first and fourth columns of keyholes 108 spaced-apart a distance 3X, as shown by the module 82 mounted to the tray section 102₁. It follows then that the module 82 depicted in FIG. 6, which has two columns of passages 86 and has feet 96 as spaced apart a distance 2X, might be keyed to the first and third columns of keyholes 108 in the tray.

As with tray 14, graphics G may be provided on the tray top wall 102a to identify the instruments or tools at the various locations in the module bases 82 supported by the tray.

Preferably, the bottom section 62 of the outer case 12 may be modified to some extent to accept the module bases 82 in that the bottom wall 62a of that section may be provided with notches or holes to provide clearance for the legs 94 and feet 96 of the module bases. If necessary, the side wall 62b of bottom section 62 may be extended below the bottom wall 62a a distance such that feet 96 of the module bases are spaced above the surface on which the case bottom section 62 is placed.

It will thus be seen that the objects set forth above, among those made apparent from the preceding description, are efficiently attained and, since certain changes may be made in the above constructions without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention described herein.

What is claimed is:

1. A medical instrument holder assembly comprising
    a holder module base including
        a plurality of first tubes having lower ends, each first tube having a wall with both an outer surface and an inner surface that defines a first passage having open upper and lower ends,
        a first web connecting the outer surfaces of the tube walls to support said first tubes in parallel spaced-apart relation so that a fluid can circulate around and between said first tubes, and
        instrument supports at the lower ends of the plurality of first tubes for supporting medical instruments placed in said first passages while allowing a fluid to circulate through said first passages, said instrument supports including narrow bridges at the lower ends of the first tubes which extend across and partially occlude the open lower ends of the first passages, and
    a cover for seating on said base so as to cover said instruments.

2. The assembly defined in claim 1 wherein the upper ends of the first passages are flared.

3. A medical instrument holder assembly comprising
    a holder module base including
        a plurality of first tubes, each first tube having a wall with both an outer surface and an inner surface that defines a first passage having open upper and lower ends,
        a first web connecting the outer surfaces of the tube walls to support said first tubes in parallel spaced-apart relation so that a fluid can circulate around and between said first tubes, and
        instrument supports at the lower ends of the plurality of first tubes for supporting medical instruments placed in said first passages while allowing a fluid to circulate through said first passages, and
    a cover for seating on said base so as to cover instruments, said cover including
        a plurality of second tubes, each second tube having a wall with both an outer and an inner surface that defines a second passage having open upper and lower ends, said lower ends having substantially the same cross-sections as the upper ends of said first passages, and
        a second web connecting the outer surfaces of the second tube walls to support the second tubes in parallel spaced-apart relation so that when the cover is seated on said base, the corresponding first and second passages are co-linear.

4. The assembly defined in claim 3 wherein the second passages are longer than the first passages.

5. The assembly defined in claim 3 wherein the upper ends of the second passages are smaller than the lower ends of the second passages.

6. The assembly defined in claim 3 wherein said base and said cover include interfitting surfaces which, when the cover is seated on the base, releasably secure the cover to the base.

7. The assembly defined in claim 1
    wherein said first web constitutes a top wall of the base, and
    further including a peripheral web extending down from said first web around said plurality of first tubes, said peripheral web consisting a side wall of the base as well as defining a seating surface for the cover.

8. The assembly defined in claim 7 wherein said base also includes a plurality of depending keys which extend below said peripheral web and are arranged to key into a surface underlying and supporting said base.

9. The assembly defined in claim 1 and further including connecting webs which connect at least some of said first tubes.

10. The assembly defined in claim 1 wherein said first web comprises a top web which extends between the upper ends of the first tubes and constitutes a top wall of the base.

11. The assembly defined in claim 10 and further including graphics formed on said top web and indicating instruments in said first passages.

12. A medical instrument holder assembly comprising
a holder module base including
- a plurality of first tubes, each first tube having a wall with both an outer surface and an inner surface that defines a first passage having open upper and lower ends,
- a first web connecting and supporting the outer surfaces of the tube walls to support said first tubes in parallel spaced-apart relation so that a fluid can circulate around and between said first tubes, and
- instrument supports at the lower ends of the plurality of first tubes for supporting medical instruments placed in said first passages while allowing a fluid to circulate through said first passages, said instruments supports including a base bottom wall supported by said first web so that the bottom wall is spaced below the lower ends of said first passages, and
- a cover for seating on said base so as to cover said instruments.

13. A medical instrument holder assembly comprising
a holder module base including
a plurality of first tubes defining first passages, each first passage having open upper and lower ends,
a first web connecting and supporting said first tubes in parallel spaced-apart relation so that a fluid can circulate around and between said first tubes, and
instrument supports at the lower ends of the plurality of first tubes for supporting medical instruments placed in said first passages while allowing a fluid to circulate through said first passages;
- a cover for seating on said base so as to cover said instruments, and an outer case, said case including
- a bottom section shaped and dimensioned to seat a plurality of said holder modules in closely packed together fashion, and
- a cover section engageable on said bottom section so as to cover said plurality of holder modules in the bottom section, said bottom section and cover section being perforated so that fluid can circulate around and into said plurality of holder modules.

14. The assembly defined in claim 13 and further including retainers in said bottom section and/or said cover section for locating and retaining the holder modules seated in the bottom section.

15. The assembly defined in claim 13 and further comprising a presentation tray, said tray having an upper wall large enough in area to support a plurality of holder modules, said upper wall including securement means for releasably securing said plurality of modules to the tray.

16. The assembly defined in claim 15 wherein the securement means include a plurality of indentations in said upper wall for snugly receiving the bases of said plurality of holder modules.

17. The assembly defined in claim 15 wherein the securement means include a plurality of keyholes in said upper wall, said keyholes being adapted to receive keys projecting from holder modules supported on the tray.

18. The assembly defined in claim 15 wherein said tray is collapsible.

19. The assembly defined in claim 18 wherein the tray comprises
- a plurality of sections, and
- interfitting surfaces on said sections for releasably securing said sections together.

20. The assembly defined in claim 15 and further including graphics formed on said upper wall indicating instruments in the holder modules supported on the tray.

* * * * *